United States Patent [19]
Ahmadzadeh

[11] Patent Number: 5,997,485
[45] Date of Patent: Dec. 7, 1999

[54] DEVICE FOR THE CONTROLLED POSITIONING OF A TROCAR OR A HOLLOW PUNCTURING NEEDLE

[76] Inventor: Massoud Ahmadzadeh, Offlumer Strasse 10, D-48485 Neuenkirchen, Germany

[21] Appl. No.: 08/727,480

[22] PCT Filed: Mar. 22, 1995

[86] PCT No.: PCT/DE95/00386

§ 371 Date: Oct. 9, 1996

§ 102(e) Date: Oct. 9, 1996

[87] PCT Pub. No.: WO95/28132

PCT Pub. Date: Oct. 26, 1995

[30] Foreign Application Priority Data

Apr. 19, 1994 [DE] Germany ............................ 44 13 520

[51] Int. Cl.⁶ ...................................................... A61B 10/00
[52] U.S. Cl. ...................... 600/567; 604/110; 604/164; 604/263; 606/171; 606/185
[58] Field of Search ...................... 604/110, 164, 604/192, 197, 198, 263, 264, 272; 606/171, 185, 188; 600/567, 562

[56] References Cited

U.S. PATENT DOCUMENTS

| | | |
|---|---|---|
| 2,269,963 | 1/1942 | Wappler ...................................... 604/61 |
| 3,538,916 | 11/1970 | Wiles . |
| 3,659,610 | 5/1972 | Cimber . |
| 4,026,288 | 5/1977 | Costa et al. . |
| 4,182,787 | 1/1980 | Goossens et al. ......................... 428/36 |
| 4,411,653 | 10/1983 | Razi . |
| 4,516,577 | 5/1985 | Scott et al. .............................. 606/188 |
| 5,048,538 | 9/1991 | Terwilliger et al. ..................... 606/171 |
| 5,067,946 | 11/1991 | Zhadanov . |
| 5,135,505 | 8/1992 | Kaufman . |
| 5,146,921 | 9/1992 | Terwilliger et al. . |
| 5,183,465 | 2/1993 | Xanthakos et al. . |
| 5,281,197 | 1/1994 | Arias et al. . |

OTHER PUBLICATIONS

"ENDOPATH Trocare Veress–Nadeln", company publication of ETHICON GmbH&Co.KG, Norderstedt/Germany, 1992.

*Primary Examiner*—Cary O'Connor
*Assistant Examiner*—Pamela L. Wingood
*Attorney, Agent, or Firm*—Paul Vincent

[57] ABSTRACT

A device (10) holds a hollow puncturing needle (11) which can be controllably moved in a first direction (16) within an aparture (21) in the device (10). The handle (14) can, when pushed, be moved in the direction of the arrow (15). If the handle (14) is moved in the direction of the arrow (15), the hollow puncturing needle (11) moves in the first direction (16). The device (10) is to be placed against a countersurface via a support surface (20). The hollow puncturing needle (11) is held in the device (10) to be axially movable controllably in the first direction (16) via the movable handle (14).

17 Claims, 3 Drawing Sheets

DEVICE FOR THE CONTROLLED POSITIONING OF A TROCAR OR A HOLLOW PUNCTURING NEEDLE

BACKGROUND OF THE INVENTION

The invention concerns a device for the controlled positioning of a trocar or a hollow puncturing needle.

This type of device has, for example, become known in the art under the designation "ETHICON ENDOPATH".

The trocar plunger of the conventional device is encased in an axially displaceable tube which also surrounds the tip of the trocar plunger in the starting position. The tube and the trocar plunger are introduced into a shaft and held therein in snapping engagement. In the event that the shaft is introduced through a tissue wall, the tube and the trocar plunger are inserted into the shaft and both components interlock with each other on the side facing away from the patient. In this configuration the trocar plunger projects beyond the free end of the shaft, wherein the tip of the trocar plunger is still completely covered and encased by the axially displaceable tube.

However, when penetration through a tissue wall or the like is effected, the patient-sided end of the shaft with the tube protruding therefrom is placed on the tissue wall and the force components exercised by the hand of the user in the axial direction cause the tip of the trocar plunger of the device to project out beyond the tube encasement to penetrate into the adjacent tissue wall. The shaft with the trocar plunger penetrates into the tissue wall with a speed depending on the strength with which the user pushes on the conventional device.

In the conventional device, a functional movement of this kind can cause uncontrolled displacement of the trocar plunger, since increased resistance requires that increased force be exercised on the shaft to cause same to penetrate through a tissue wall. If however, the resistance suddenly decreases, it is possible that the utilized force components causing the axial displacement are not simultaneously reduced so that the shaft exercises an axial motion which is greater than that desired.

Known in the art from U.S. Pat. No. 5,067,946 is an injury avoiding needle device with which a needle can be pushed out of a housing using an indexing wheel. The needle is utilized in association with blood transfusion and intravenous applications. The indexing wheel has teeth which engage in teeth of a mounting, holding the needle, which is axially displaceable in the device. The needle is displaced by rotation of the indexing wheel.

Known in the art from U.S. Pat. No. 2,269,963 is an implantation device with which radioactive capsules can be released in a controlled fashion from a magazine in a hollow region. The pipe filled with the capsules must be capable of insertion by hand into the hollow region against possible resisting forces. When the free end of the pipe is positioned as desired one or more capsules can be released in a controlled fashion.

U.S. Pat. No. 5,183,465 describes a device with which a needle or a trocar can be introduced through the abdominal wall. The needle or the trocar are held and displaced within a mounting frame. The mounting frame with the needle is placed on the abdominal wall from the outside and a screw is attached in a rotatable fashion on the mounting frame, the free end of which cooperates with the needle or with the trocar. Upon turning in one rotational direction, the screw is displaced into the mounting and thereby pushes the needle or the trocar out of the mounting. In order for the tip of the needle or of the trocar to overcome a resistance of greater or lesser extent, a turning of the adjustment screw with correspondingly different strength is necessary.

It is therefore the purpose of the present invention to develop a device for controlled placement of a trocar or of a hollow puncturing needle which does not require different force application by the user of the device, rather which facilitates an even axial motion of the shaft with the trocar plunger independent of the resistive force working against the trocar plunger.

SUMMARY OF THE INVENTION

This purpose is achieved in accordance with the invention in that the trocar or the hollow puncturing needle is held in the device in an axial displaceable fashion and is stepwise movable in the first direction relative to a support surface of the device via activation means having a fixed handle and a movable handle, wherein the displacement path of the movable handle relative to the fixed handle defines the length of the travel path of the trocar or of the hollow puncturing needle in a first direction towards the patient.

In this fashion the device in accordance with the invention has the substantial advantage that arbitrary trocar systems can always be positioned by the user with constant expenditure of force independent of their size, that is to say independent of the magnitude of the shaft diameter. The device in accordance with the invention can be safely placed at the desired location via the support surface and the trocar or the hollow puncturing needle are moved by means of the activation means. Resistive forces of various strength associated with the utilization of the trocar or of the hollow puncturing needle can be overcome in dependence on the means used for displacing the device and in dependence on the device components provided for force transfer. The support surface is normally substantially larger than the trocar which is to be positioned so that a secure support is created to always facilitate penetration of the trocar at the desired location. An unintentional slipping of the device during insertion of the trocar into the tissue wall is thereby safely prevented. The activation means can be moved mechanically or by means of a motor so that the device in accordance with the invention is suitable for a wide range of applications with continuously constant force expenditure on the part of the user.

The activation means have a fixed handle and a movable handle, wherein the length of the travel path of the trocar or of the hollow puncturing needle in a direction towards the patient is defined by the displacement path of the movable handle relative to the fixed handle.

This has the advantage that an exact travel path of the trocar or of the hollow puncturing needle is determined via the operation of the handles. The handles are fashioned in such a manner that they are adapted to hand operation by the user and can be displaced without large expenditure of force. Towards this end a large handle displacement path could correspond to a short travel path for the trocar or hollow puncturing needle. The transmission ratio between the displacement path of the handle and the travel path of the trocar or of the hollow puncturing needle can be freely chosen.

In further embodiments of the invention the trocar or the hollow puncturing needle to be positioned can be introduced into an opening of the device and displaced through the device. In addition, via displacements of the movable handle towards the fixed handle, the trocar or the hollow puncturing needle can be chocked with sections of an opening of a plate which is displaceable via the movable handle and the trocar or the hollow puncturing needle can be moved in the first direction via displacements of the plate.

This has the advantage that conventional trocars, trocar systems, or hollow puncturing needles can be utilized with the device in accordance with the invention. The trocar is introduced into the device in accordance with the invention and is moved in the axial direction via the device in accordance with the invention. A particularly simple and effective movement of the trocar in the axial direction is achieved when a plate surrounds the trocar during an axial displacement thereof so that the trocar can be displaced in an axial direction by frictional forces between the trocar and the plate. The plate of the device in accordance with the invention is pivoted in such a fashion that the edges of an opening in the plate are chocked with the outer peripheral surface of the trocar and the trocar is moved in the first direction by further pivoting of the plate.

In a further embodiment of the invention, the plate is loaded in a second direction opposite to the first direction and the maximum displacement of the plate is limited by the displacement path between the movable handle and the fixed handle.

This has the advantage that the plate is always automatically pushed by the spring into a position in which a trocar or a hollow puncturing needle can be guided into the device in accordance with the invention and through the opening in the plate without jamming. The spring likewise restores the plate to its original position (neutral position). The plate can only be displaced in opposition to the spring force by means of the handles. In this fashion a pressure point is created which must be overcome by the user to axially displace the trocar or the hollow puncturing needle.

In further preferred embodiment of the invention the device can be swung-open at the upper side to provide access to the opening.

This has the advantage that, after a trocar or a hollow puncturing needle has been positioned, the device can then be easily removed from the positioned trocar or from the positioned hollow puncturing needle when the end of the trocar or of the hollow puncturing needle facing away from the patient is larger than the opening in the device in accordance with the invention through which the trocar or the hollow puncturing needle is introduced.

In a further embodiment of the invention the device has a mounting formed on the housing of the device opposite to the handles.

This has the advantage that the trocar or the hollow puncturing needle can be kept securely guided during the course of a positioning procedure and the device in accordance with the invention cannot slip out of its desired position.

In a further embodiment of the invention, the trocar or the hollow puncturing needle has recesses on a limited outer section along the axial extent which engage in snap elements of the device, wherein the first snap element is attached to the moving handle and is pivotable with the moving handle and the second snap element is arranged on the fixed housing of the device.

This configuration has the advantage that, in an additional embodiment of the device in accordance with the invention, the axial placement of a trocar can be safely effected in the event that same has recesses which cooperate with snap elements of the device. The snap elements have a diagonal ramp and are spring-loaded in such a fashion that they are always automatically urged back into their initial position from which the axial motion of the trocar or of the hollow puncturing needle is initiated. The second snap element functions to hold the trocar or the hollow puncturing needle in the corresponding position and to prevent an uncontrolled motion of the trocar or of the hollow puncturing needle opposite to the first direction.

In a further embodiment of the invention the trocar or the hollow puncturing needle can be borne in a stationary fashion in an axially displaceable carriage of the device at the end facing away from the patient, the carriage being displaceable within the device along paths of arbitrary predetermined length, the trocar or the hollow puncturing needle exiting from the device at the patient-sided end during travel of the carriage in the first direction with the support surface from which the trocar or the hollow puncturing needle projects during travel in the first direction being formed on one end of the device and a stationary and a movable handle are disposed at the other end, wherein the displacement of the carriage in the first direction can be activated via the movable handle.

This has the advantage that only the carriage and the support surface must be adapted to the trocar or to the hollow puncturing needle being positioned. In this embodiment of the device in accordance with the invention a wide support surface is possible to facilitate a secure seating on the tissue wall. The device is configured in such a fashion that the trocar or the hollow puncturing needle is completely borne within the device in the initial position so that there is no danger of injury during handling of the device in the event that the tip of the trocar plunger or of the hollow puncturing needle are not separately covered. When the activation means move, the trocar or the hollow puncturing needle leave the device with the predetermined step sizes and penetrate into the immediately adjacent tissue wall. After termination of the positioning the carriage is opened and the device is separated from the trocar or from the hollow puncturing needle.

A stationary and a movable handle are formed on the end of the device facing away from the patient, wherein the stepwise or continuous displacement of the carriage in the first direction can be triggered by the movable handle. In this fashion the trocar or the hollow puncturing needle can be axially moved precisely in the smallest of steps.

In further embodiments of the invention the carriage is borne and guided in a device housing having a shape of a half-shell and the carriage has a tensioning device for the end of the trocar or of the hollow puncturing needle facing away from the patient.

This has the advantage that the carriage can be safely and effectively axially moved and guided in a directed manner using simple and easily accessible means. The tensioning device provides for the secure mounting, rapid aligned securing in as well as removal from the tensioning device of trocars or of a hollow puncturing needle having ends of arbitrary shape.

In an improvement of the device in accordance with the invention the half-shell-shaped housing is borne at the end facing away from the patient for rotation about the longitudinal axis of the device in the direction of arrows.

This has the advantage that the trocar plunger tip or the hollow puncturing needle tip can be directed independent of the position of the device. In this fashion the activation means can be positioned relative to the user in as convenient a manner as possible.

In a further embodiment of the device in accordance with the invention a guiding rod, having a fixed connection to the carriage, can be displaced via the displacement path of the movable handle relative to the stationary handle. The guiding rod facilitates the precise guiding of the carriage and the guiding rod can be configured to facilitate the transfer of force from the activation means to the carriage independent of the configuration of the trocar or of the hollow puncturing needle being positioned. The axial displacement motion of the trocar is not directly transferred to the trocar or to the hollow puncturing needle, rather to the carriage which holds the trocar or the hollow puncturing needle.

In a further embodiment of the invention the positioning rod is held without displacement in each position and is only movable in the first direction via the activation means.

This has the advantage that the trocar or the hollow puncturing needle cannot be moved unintentionally opposite to the first direction during placement of the trocar or of the hollow puncturing needle. Even if the placement procedure is interrupted, the trocar or the hollow puncturing needle remain at the position into which they had been placed.

A particularly secure guiding of the trocar or of the hollow puncturing needle is facilitated when the support surface has a guiding section, for example a recess, in which the trocar or the hollow puncturing needle is guided. The trocar seats at two bearing points during the entire positioning procedure.

In further embodiments of the device in accordance with the invention, the handles have an unlocking mechanism, for example a lever, which facilitates a displacement of the carriage in a second direction when activated.

This has the advantage that the guiding rod with the carriage can be pulled back when the unlocking mechanism is activated. In the event that the lever is released out of chocked position relative to the guiding rod, it is possible to move the guiding rod opposite to the positioning direction. The lever is spring-loaded in such a fashion that it always permits for motion of the guiding rod in the positioning direction but prevents motion in the second direction. The guiding rod can then only be moved in the second direction when the lever is unlocked in opposition to its spring load.

In a preferred embodiment of the invention the carriage has recesses into which the end of the trocar or of the hollow puncturing needle facing away from the patient can be seated in a largely interlocking fashion and the trocar or the hollow puncturing needle is kept guided stably directed in the recesses via a quick acting closure. Various exchangeable inserts can be provided for in the carriage which are each adapted to the end of a trocar or of a hollow puncturing needle facing away from the patient. In this fashion the device in accordance with the invention can be widely used in combination with conventional trocar systems or hollow puncturing needles.

It is also possible for the carriage and/or support surface to be mounted in the device in an exchangeable fashion. In the event that the support surface is also exchangeable a support surface can be utilized having a recess adapted to the corresponding trocar or hollow puncturing needle being positioned, depending on need.

In the event that a spacer is disposed between the carriage and the activation means the end position of the carriage can always be easily selected. In the unlocked position, the carriage is drawn back up to abutment with the spacer. The carriage is then located in a position in which it can fully accept a trocar or a hollow puncturing needle; that is to say the patient-sided end of the trocar or of the hollow puncturing needle does not project beyond the device.

In the event that the described device is produced from steam-sterilizable materials and if the individual components of the device are disposed in a visible and accessible fashion same can be cleaned rapidly and effectively. The device can thereby be utilized a plurality of times.

Further advantages can be derived from the description and the accompanying drawing. The features mentioned above and those to be described further below can be utilized in accordance with the invention individually or collectively in arbitrary combination. The embodiments mentioned are not to be understood as exhaustive enumeration rather have exemplary character only.

The invention is represented in the drawing and will be more closely explained with embodiments in the drawing.

DESCRIPTION OF THE PREFERRED EMBODIMENT

The figures show the object in accordance with the invention in a highly schematic manner and are not to be taken to scale.

Figure 1:
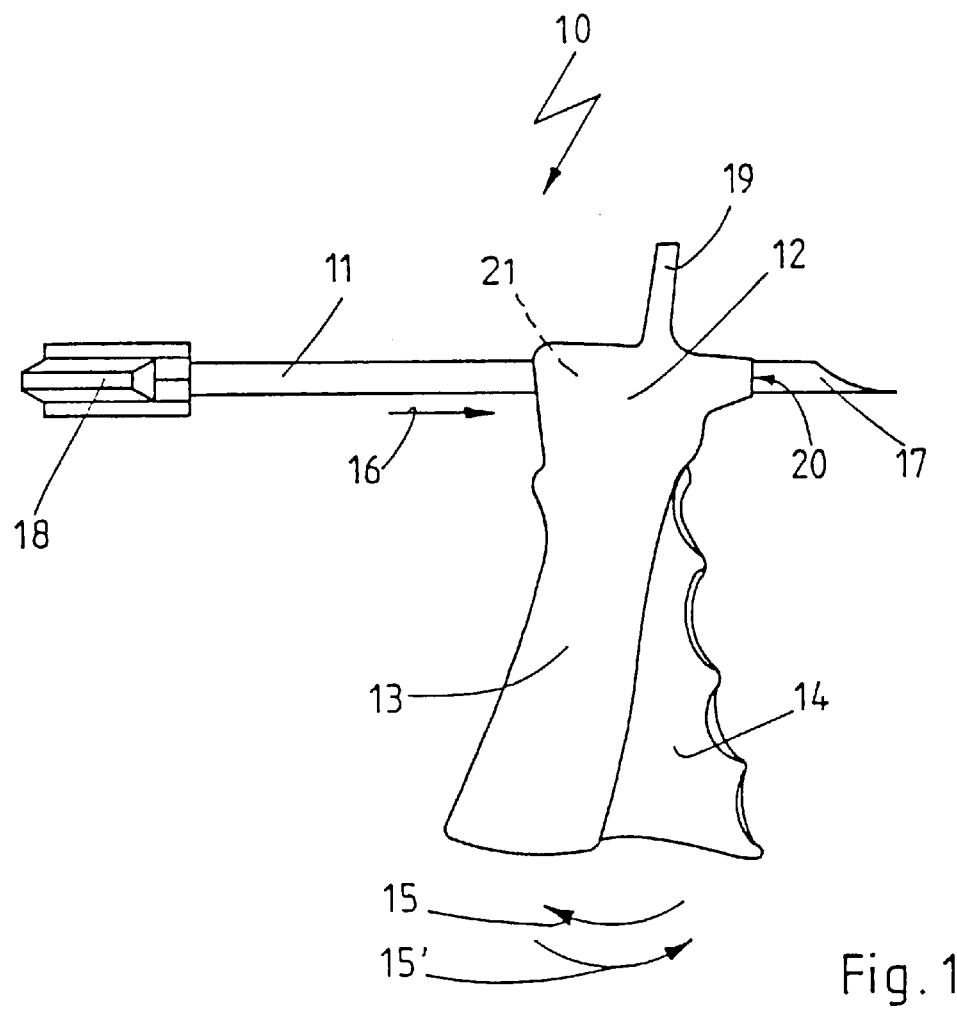
FIG. 1 shows a device in accordance with the invention for positioning a hollow puncturing needle, wherein a conventional hollow puncturing needle has been introduced into the device.

FIG. 1 shows a device 10 for controlled positioning of a hollow puncturing needle 11. The device 10 has a housing 12, having a fixed handle 13 disposed thereon. A movable handle 14 is mounted in the stationary handle 14. The movable handle 14 can be moved towards the stationary handle 13 in the direction of arrow 15 in opposition to a spring force. The movable handle 14 moves load-relieved automatically in the direction of arrow 15'.

The hollow puncturing needle 11 which is to be positioned can be inserted into the housing 12 in a first direction 16. The hollow puncturing needle 11 itself has a tip 17 directed towards the patient and the hollow puncturing needle 11 has a wing-shaped end 18 at the end facing away from the patient.

Furthermore, a handle 19 is formed on the housing 12 and a support surface 20 is formed on the device 10 at the side facing the patient. The device 10 has an aperture 21 into which the hollow puncturing needle can be inserted. In the event that the hollow puncturing needle 11 is inserted into the aperture 21 it penetrates through an opening 22 in a plate 23 which cooperates with the movable handle 14. When the movable handle 14 is moved in the direction 15 towards the fixed handle 13, the hollow puncturing needle 11 is displaced in the first direction 16.

Figure 2:
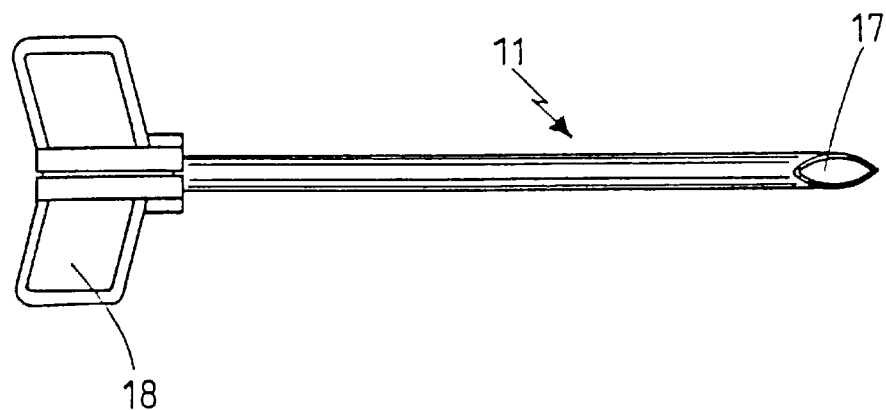
FIG. 2 shows a hollow puncturing needle as utilized in FIG. 1.

FIG. 2 shows an overall view of a hollow puncturing needle 11 utilized in FIG. 1. The conventional hollow puncturing needle 11 is a hollow needle and has a tip 17 on the side facing the patient. The end of the hollow puncturing needle 11 diametral thereto is wing-shaped 18. The wings can be swung-open with little expenditure of force. In this fashion the hollow puncturing needle 11 is axially split in a conventional fashion.

Figure 3:
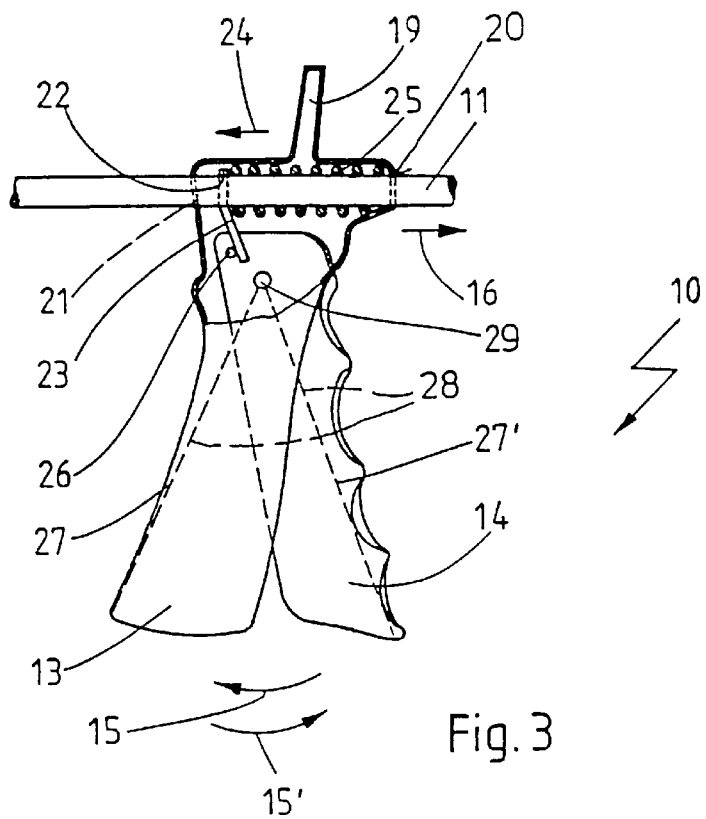
FIG. 3 shows a functional representation of the device according to FIG. 1, wherein the device in accordance with the invention is shown partially in a cut-away fashion.

FIG. 3 shows the principle of operation of the device 10 as shown in FIG. 1.

Only that section of the hollow puncturing needle 11 which penetrates the device 10 is shown.

When the device 10 is applied the hollow puncturing needle 11 is retracted to a sufficient extent that it does not protrude beyond the support surface 20. The support surface 20 is placed on a counter-surface. Subsequent thereto the user holds the device 10 with one hand at the handles 13, 14 and with the other hand at the mounting 19. When the handles 13, 14 are pressed together the hollow puncturing needle 11 moves in the first direction 16. It is possible, in the handle position shown in FIG. 3, for the hollow puncturing needle 14 to be retracted in the second direction 24. The hollow puncturing needle 11 is surrounded in the device 10 by the opening 22 of plate 23. The plate 23 is pressure loaded by a spring 25. The spring loading acts opposite to the first direction 16. The plate 23 is connected in a movable fashion to a pin 26 of the movable handle 14. When the handles 13, 14 are pushed together the outer contour of opening 22 is chocked with the outer peripheral surface of the hollow puncturing needle 11 to guide the hollow puncturing needle 11, in frictional engagement, in the first direction 16. When the handles 13, 14 are load-relieved the movable handle 13 is pushed into the position shown in FIG. 3 by means of the leg 27, 27' of a spring 28 held by bearing 29. In this fashion the plate 23 is retracted and the plate 23 is pushed into a starting position via the spring 25. If the handles 13, 14 are then once more pressed together, the hollow puncturing needle 11 is again displaced via the plate 23 in the first direction 16.

Figure 4:
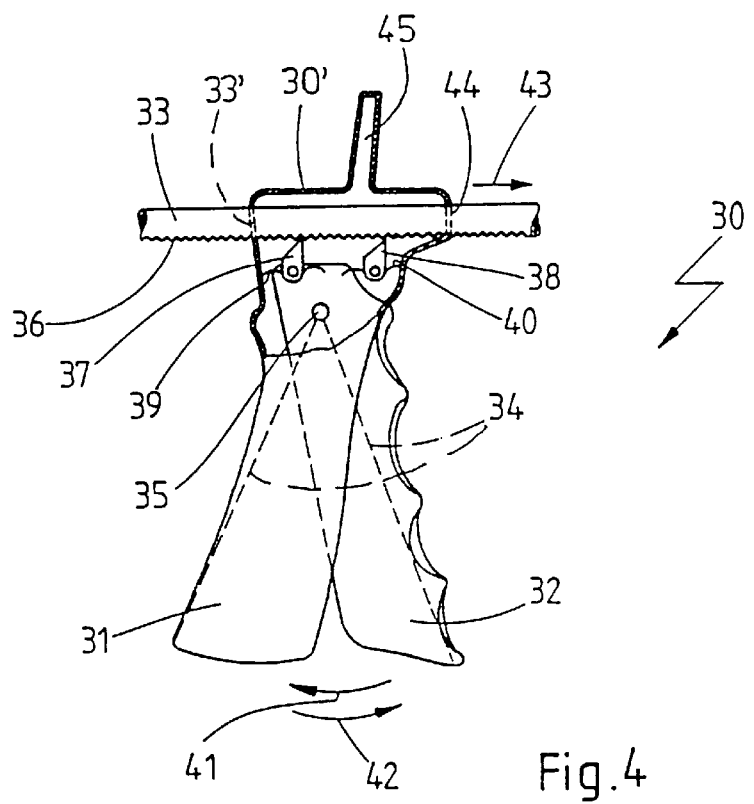
FIG. 4 shows a further functional principle of a device in accordance with the invention for placement of a trocar or of a hollow puncturing needle having recesses.

FIG. 4 shows a further embodiment of a device 30 shown in a partially cut-away manner. The device 30 comprises a housing 30' having a stationary handle 31 and a movable handle 32.

The device 30 can be utilized to position a hollow puncturing needle 33 in a controlled manner. The hollow puncturing needle 33 can be introduced into an aperture 33' of the housing 30'. The handles 31, 32 are pushed apart via a spring 34 held in a bearing 35.

The device 30 can be utilized to position hollow puncturing needles 33 or trocar systems having recesses 36. The recesses 36 must be formed over at least a partial section at the outer periphery of the hollow puncturing needle 33. The recesses 33 engage in snap elements 37, 38 which are loaded by spring means 39, 40. The snap element 37 is connected to the movable handle 32 and the snap element 38 is borne in housing 30'. The movable handle 32 can be moved in the direction of arrow 41 or 42. In the event that the handle 32 is moved in the direction of arrow 41, the hollow puncturing needle 33 moves in a first direction 43.

If a hollow puncturing needle 33 is to be positioned with the device 30, the device 30 is placed on the desired counter-surface via support surface 44. A user holds the device 30 at the handles 31, 32 and at a mount 45. When the handles 31, 32 are pressed together the hollow puncturing needle 33 is guided via the snap element 37 in the direction of arrow 43. The stationary mounted snap element 38 likewise moves in the direction of arrow 43. When the movable handle 32 is pivoted in the direction of arrow 42, the snap element 37 travels back into its initial position via a diagonal surface configured on the snap element 37 and snaps at this location into a recess 36 of the hollow puncturing needle 33. If the handles 31, 32 are then once more pressed together, the hollow puncturing needle 33 can again be positioned in the first direction 43.

Figure 5:
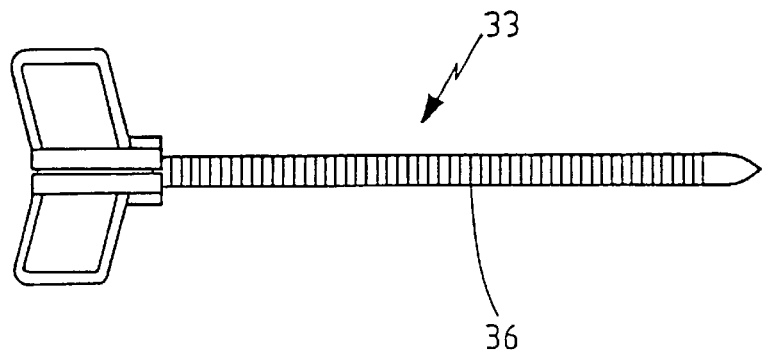
FIG. 5 shows a hollow puncturing needle as, for example, utilized in the device according to FIG. 4.

FIG. 5 shows the hollow puncturing needle 33 from below as utilized in the device 30. The hollow puncturing needle 33 has recesses 36 formed on the underside which can engage in the device 30 in snap elements 37, 38. The hollow puncturing needle 33 can, if necessary, be split in the axial direction by means of the wings on the end of the hollow puncturing needle 33 facing away from the patient.

The devices shown in FIGS. 3 and 4 can, if necessary, be opened in the upper side region (this is not shown in FIGS. 3 and 4) so that after positioning of the hollow puncturing needle the device can be separated from the positioned hollow puncturing needle.

Figure 6:
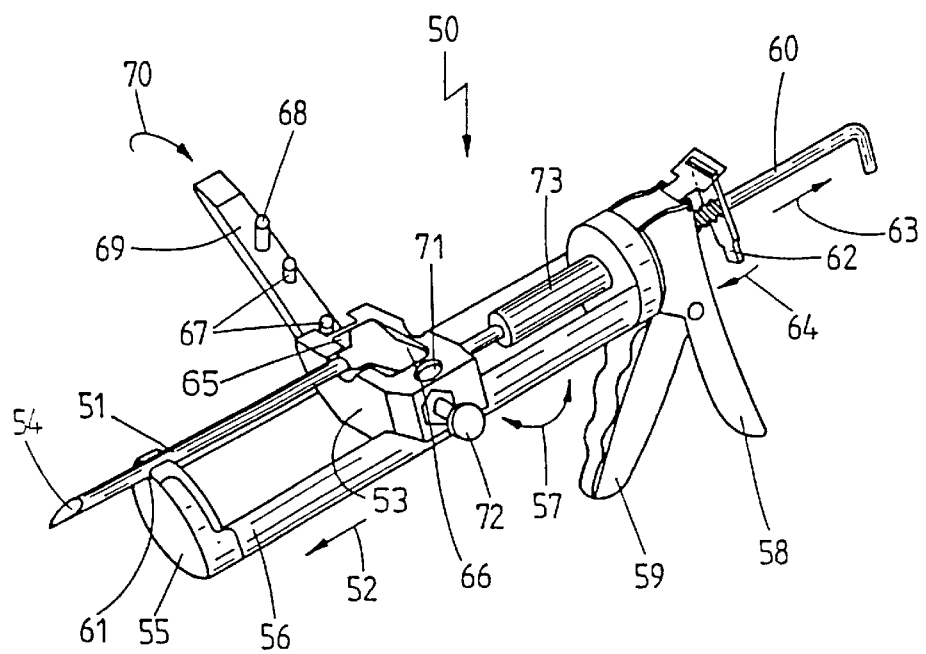
FIG. 6 shows a further embodiment of a device in accordance with the invention for placement of a trocar or of a hollow puncturing needle in perspective view.

FIG. 6 shows a further embodiment of a device 50 in accordance with the invention for the controlled positioning of the hollow puncturing needle 51 or of a trocar. The device 50 can be used to position the hollow puncturing needle 51 in a first direction 52 in a controlled fashion. The hollow puncturing needle 51 is mounted in a movable carriage 50 at the end facing away from the patient. The hollow hollow puncturing needle 51 seats on a support surface 55 via a tip 54. The support surface 55 is held in an exchangeable fashion in a half-shell-shaped housing 56 of the device 50. The half-shell-shaped housing 56 can be rotated in the direction of arrow 57. A first stationary handle 58, in which a second movable handle 59 is borne, is disposed on the device 50. The movable handle 59 can displace a guide rod 60 in the direction of arrow 52 when moved. A recess 61 is formed in the support surface 55 to constitute a guide for the hollow puncturing needle 51.

The guide rod 60 penetrates through a lever 62 in the device 50, the lever 62 keeping the guide rod 60 in its instantaneous position. The guide rod 60 can then be moved in a second direction 63 by hand when the lever 62 is pivoted in the direction of arrow 64 against the force of a spring (unlocked).

The guide rod 60 is connected to the carriage 53 which can be moved in a guided fashion within the half-shell-shaped housing 56 inside the housing 56. When the guide rod 60 is moved, the carriage 56 is also moved. Recesses 65 are formed in carriage 53 for a wing-shaped end 66 of the hollow puncturing needle 51. The recesses 65 can be of arbitrary contour, that is to say the recesses 65 can also be configured for exchangeability so that arbitrary ends of trocar systems can be seated in the recesses 65 in as interlocking a fashion as possible. That end of a hollow puncturing needle or of a trocar facing away from the patient is held in the recesses 65 via positioning pins 67 when a locking pin 68 of a plate 69 is fixed in an opening 71, pivoted in the direction of arrow 70, by a displaceable pin 72. The displaceable pin 72 can be utilized to unlock the plate 69 if necessary and the plate 69 can be pivoted once more in a direction opposite to that of arrow 70. The positioned hollow puncturing needle or the positioned trocar can then be removed from the recess 65.

A spacer 73 is provided for on the guide rod 60 inside of the half-shell-shaped housing 56 to define an end position of the carriage 53. The spacer 73 is adapted to the length of a hollow puncturing needle or trocar to be positioned. The device according to FIG. 6 has a pivotable plate inside the handles 58, 59 as, for example, shown and described in FIG. 3. The lever 62 is pushed, via a spring, into a position which prevents movement of the guide rod 60 in the direction of arrow 63 when the lever is spring-loaded. The guide rod 60 can be moved in the direction of arrow 63 when the lever 62 is displaced in opposition to the spring-loading.

A device 10 holds a hollow puncturing needle 11 which can be controllably moved in a first direction 16 within an aperture 21 in the device 10. The handle 14 can, when pushed, be moved in the direction of the arrow 15. If the handle 14 is moved in the direction of arrow 15, the hollow puncturing needle 11 moves in the first direction 16. The device 10 is to be placed against the counter-surface via a support surface 20. The hollow puncturing needle is held in the device 10 to be axially movable controllably in the first direction 16 via the movable handle 14.

We claim:

1. A device for controlled positioning of a puncturing means into a patient, the puncturing means having a recess in a limited outer pheripheral section along an axial extend thereof, the device comprising:

a housing for holding the puncturing means in an axially displaceable manner, said housing having a support surface adjacent to the patient;

activation means mounted to said housing for stepwise movement of the puncturing means towards the patient, said activation means having a fixed handle and a movable handle, a displacement path between said fixed and said movable handle defining a travel path length of the puncturing means towards the patient;

a first snap element attached to said movable handle for pivoting with said movable handle and engaging said puncturing means recess; and second snap means mounted on said housing and engaging said puncturing means recess.

2. The device of claim 1, wherein the housing has an aperture into and through which the puncturing means is positioned and further comprising plate means mounted in said housing and connected between puncturing means and said activation means to move the puncturing means towards the patient when said movable handle is displaced towards said fixed handle.

3. The device of claim 2, further comprising plate spring means for biasing the plate in a direction opposite to the patient, wherein a maximum displacement of said plate is limited by said displacement path.

4. The device of claim 1, wherein said housing is adapted to open at an upper side thereof for providing access to said aperture.

5. The device of claim 1, further comprising a mounting integral with said housing opposite to said activation means.

6. The device of claim 1, further comprising activating spring means for holding apart said activation means, said activation means being pushed together for moving the puncturing means towards the patient in opposition to a force of said activation spring means.

7. A device for controlled positioning of a puncturing means into a patient comprising:

a housing for holding the puncturing means in an axially displaceable manner, said housing having a support surface adjacent to the patient;

activation means mounted to said housing for stepwise movement of the puncturing means towards the patient, said activation means having a fixed handle and a movable handle, a displacement path between said fixed and said movable handle defining a travel path length of the puncturing means towards the patient; and a carriage mounted in the housing for continuous axial motion therein, the puncturing means being borne within said carriage in a stationary manner at a puncturing means end facing away from the patient, said fixed and said movable handle being disposed at a housing end facing away from the patient, said carriage communicating with said movable handle to displace the puncturing means beyond said support surface towards the patient when said movable handle is moved.

8. The device of claim 7, wherein said housing has a half-shell shape within which said carriage is borne in a guided fashion, and wherein said carriage comprises tensioning means communicating with said puncturing means end.

9. The device of claim 8, wherein said half-shell-shaped housing is adapted for rotation about a longitudinal axis at said housing end.

10. The device of claim 7, further comprising a guide rod communicating with said movable handle for displacement thereby, said guide rod having a fixed connection to said carriage.

11. The device of claim 10, wherein said guide rod is mounted in said housing without slippage at positional locations, said guide rod being moved exclusively via said activation means towards the patient.

12. The device of claim 7, wherein said support surface comprises a guiding section for holding the puncturing means in a displaceable and guided fashion.

13. The device of claim 7, wherein said activation means comprises an unlocking mechanism for directing displacement of said carriage in a direction away from the patient.

14. The device of claim 7, wherein said carriage has a recess for interlocked insertion of said puncturing means end, and further comprising quick acting closure means for holding and guiding the puncturing means in said carriage recess.

15. The device of claim 7, wherein at least one of said carriage and said support surface are adapted for replacement and exchange.

16. The device of claim 7, further comprising a spacer between said carriage and said activation means.

17. The device of claim 1, wherein the device consists essentially of steam-sterilizable materials arranged and adapted for disassembly, cleaning, and re-assembly.

* * * * *